US007608412B2

(12) United States Patent
Wooten et al.

(10) Patent No.: US 7,608,412 B2
(45) Date of Patent: Oct. 27, 2009

(54) P62 AS A DIAGNOSTIC TOOL FOR ALZHEIMER'S DISEASE

(75) Inventors: Marie W. Wooten, Auburn, AL (US); Maria T. Diaz-Meco, Cincinnati, OH (US); Jorge Moscat, Cincinnati, OH (US)

(73) Assignee: Auburn University, Auburn, AL (US)

( * ) Notice: Subject to any disclaimer, the term of this patent is extended or adjusted under 35 U.S.C. 154(b) by 127 days.

(21) Appl. No.: 11/539,035

(22) Filed: Oct. 5, 2006

(65) Prior Publication Data
US 2007/0238643 A1    Oct. 11, 2007

Related U.S. Application Data

(60) Provisional application No. 60/723,782, filed on Oct. 5, 2005.

(51) Int. Cl.
*G01N 33/567* (2006.01)
*G01N 33/53* (2006.01)
*G01N 33/537* (2006.01)
*G01N 33/566* (2006.01)

(52) U.S. Cl. .................. 435/7.21; 435/7.1; 435/7.9; 435/7.92; 436/503; 436/501

(58) Field of Classification Search .................. None
See application file for complete search history.

(56) References Cited

FOREIGN PATENT DOCUMENTS

| WO | WO 97/22255 | 6/1997 |
| WO | WO 2005/050170 | 6/2005 |

OTHER PUBLICATIONS

Schenk et al., 1995, J. Med. Chem., vol. 38, No. 21, pp. 4141-4154.*
Database Biosis [Online] Biosciences Information Service, Philadelphia, PA US; 2003, C.Y. Shao et al. "Association of PKCiota/lambda, p62 and ubiquitin with inclusions of neurodegenerative disease."
E. Kuusisto et al. "Early accumulation of p62 in neurofibrillary tangles in Alzheimer's disease: Possible role in tangle formation," Neuropathology and Applied Neurobiology, vol. 28, No. 3, Jun. 2002, pp. 228-238.
K. Zatloukal et al. "P62 is a common component of cytoplasmic inclusions in protein aggregation diseases," American Journal of Pathology, Philadelphia, PA, vol. 160, No. 1, Jan. 2002 pp. 255-263.
E. Kuusisto et al. "Ubiquitin-binding protein P62 is present in neuronal and glial inclusions in human tauopathies and synucleinopathies," Neuroreport Rapid Communications of Oxford, Oxford, Great Britain, vol. 12, No. 10, Jul. 20, 2001, pp. 2085-2090.
Carolin Lackner et al. "p62 protein is expressed in pancreatic beta cells" Journal of Pathology, vol. 206, No. 4, Aug. 2002(Aug. 2005), pp. 402-408.
H. Lage et al. "Expression of a glypican-related 62-kDa antigen is decreased in hepatocellular carcinoma in correspondence to the grade of tumor differentiation," Virchows Archive, Springer International, Berlin, DE, vol. 438, No. 6, Feb. 21, 2001, pp. 567-573.

Nagaoka Utako at al. "Increased expression of p62 in expanded polyglutamine-expressing cells and its association with polyglutamine inclusions" Journal of Neurochemistry, vol. 91, No. 1, Oct. 2004, pp. 57-68.
Nakano Toshiya et al. "Expression of ubiquitin-binding protein p62 in ubiquitin-immunoreactive intraneuronal inclusions in amyotrophic lateral sclerosis with dementia: analysis of five autopsy cases with broad clinicopathological spectrum," Acta Neuropathologica Apr. 2004, vol. 107, No. 4, Apr. 2004, pp. 359-364.
Angelina Rodriguez, et al. "Mature-onset obesity and insulin resistance in mice deficient in the signaling adapter p62" Cell Metabolism, vol. 3, No. 3, Mar. 2006, pp. 211-222.
Andorfer, C, and Y. Kress, et al. (2003) *Hyperphosphorylation and aggregation of tau in mice expressing normal human tau isoforms.* . Neurochem. 86, 582-590.
Babu, J., T. Geetha, & M. Wooten (2005) *Sequestosome 1/p62 shuttles polyubiquitinated tau for proteasomal degradation.* J. Neurochem. 94, 192-203.
Bennett, E.M., N.P. Bence, et al. (2005) *Global Impairment of the ubiquitin proteasome system by nuclear or cytoplasmic protein aggregates precedes inclusion body formation.* Mol. Cell 17, 351-365.
Busciglio, J., A. Lorenzo, et al. (1995) *Beta-amyloid fibrils induce tau phosphorylation and loss of microtubule binding.* Neuron 14, 879-888.
Capsoni, S., G. Comparini, et al. (2000) *Alzheimer-like neurodegeneration in aged anti-nerve growth factor transgenic mice.* Proc. Natl. Acad. Sci. USA 97, 6826-6831.
Chang, S., J.H. Kim, & J. Shin, (2002) *P62 forms a ternary complex with PKCC and PAR-4 and antagonizes PAR-4 induced PKCC inhibition.* FEBS Lett. 510, 57-61.

(Continued)

*Primary Examiner*—Olga N Chernyshev
(74) *Attorney, Agent, or Firm*—Andrus, Sceales, Starke & Sawall, LLP

(57) ABSTRACT

The p62 protein has been analyzed and identified as the significant contributor to several metabolic pathways that lead to metabolic syndrome, Alzheimer's Disease, and other related diseases. The absence of the p62 protein has a profound effect on the accumulation of tau protein, amyloid beta protein and an increase in blood insulin levels. The accumulation of tau protein and amyloid beta protein in neurological tissues is a hallmark of neurological metabolic diseases such as Alzheimer's Disease and related dementias. Moreover, increase blood insulin levels is an indicator of insulin resistance in mammals. Accordingly, the present invention provides a method for screening a mammal for metabolic disease comprising the step of detecting the absence of the p62 protein. The present invention also contemplates a method of screening a mammal for a metabolic syndrome comprising the steps of detecting the level of p62 protein in a metabolic pathway and determining whether the level of p62 protein falls below a threshold level. A pharmaceutical composition is also contemplated for therapeutic supplementation of a metabolic pathway, the pharmaceutical composition comprising a p62 protein or an amide, ester or salt thereof and a pharmaceutically effective carrier. Such pharmaceutical composition will have an inhibitory action on the phosphorylation, ubiquitination, accumulation of tau protein, an inhibitory effect on the accumulation of APP/amyloid beta and may operate to lower blood insulin levels.

3 Claims, 6 Drawing Sheets

OTHER PUBLICATIONS

Dou, F., W. Netzer, et al. (2003) *Chaperones increase association of tau protein with microtubules*. Proc. Natl. Acad. Sci. USA 2, 721-726.

Duran, A., M. Serrano, et al. (2004) *The atypical PKC-interacting protein p62 is an important mediator of RANK-activated osteoclastogensis*. Dev. Cell 6, 303-309.

Etlene-Mannerville, S. & A. Hall, (2003) *CDC42 regulates GSK3β and adenomatous polyposis coli to control cell polarity*. Nature 421, 753-756.

Gallyas, F., (1971) *Silver staining of Alzheimer's neurofibrillary changes by means of physical development*. Acta Morphol. Acad. Sci. Hung 19, 1-8.

Greetha, T. & M.W. Wooten, (2003) *Association of the atypical protein kinase C-interacting protein p62/ZIP with nerve growth factor TrkA regulates receptor trafficking and Erk5 signaling*. J. Biol. Chem. 278, 4730-4739.

Gerber, S., J. Rush, et al. (2003) *Absolute quantification of proteins and phosphoproteins from cell lysates by tandem MS*. Proc. Natl. Acad. Sci. USA 100, 6940-6945.

Godermann, R., J. Biernat, E.Mandelkow (1999) *Phosphorylation of tau proteins by recombinant GSK3β: pronounced phosphorylation at select Ser/Thr-Pro motifs but no phosphorylation at Ser 262 in the repeat domain*. FEBS Lett. 454, 157-164.

Gotz, J., F. Chen, J. van Dorpe & R. M. Nitsch. (2001) *Formation of neurofibrillary tangles in P301L tau transgenic mice induced by Aβ42 fibrils*. Science 293, 1491-1495.

Gotz, J., F. Chen, et al. (2001) *Tau filament formation in transgenic mice expressing P301L tau*. J. Biol. Chem. 276, 529-534.

Greenburg, S.G. & P.A. Davis, (1990) *A preparation of Alzheimer paried helical filaments that displays distinct τ proteins by polyacrylamide gel electrophoresis*. Proc. Natl. Acad. Sci. USA 87, 5827-5831.

Guntern, R., C. Bouras, P.R. Hoff & P.G. Vallet, (1992) *An improved thioflavine-S method for staining neurofibrillary tangles and sensile plaques in Alzheimer's disease*. Experientia. 48, 8-10.

King, G.D. & R.S. Turner, (2004) *Adaptor protein interactions: modulators of amyloid precursor protein metabolism and Alzheimer's disease risk?* Exp. Neurol. 185, 208-219.

Lione, L.A., R.J. Carter, et al. (1999) *Selective discrimination learning impairments to mice expressing the human Huntington's disease mutation*. J.Neurosci. 19, 10428-10437.

Li, B., R. Ryder, et al., (2004) *Overexpression of GSK3BS9A resulted in tau hyperphosphorylation and morphology reminiscent of pretangle-like neurons in the brain of PDGSK3β transgenic mice*. Transgenic Res. 13, 385-396.

Oddo, S., A. Caccamo, et al. (2003)*Triple-transgenic model of Alzheimer's disease with plaques and tangles: intracellular Aβ and synaptic dysfunction*. Neuron 39, 409-421.

Peng, J., D. Schwartz, et al. (2003) *A proteomics approach to understanding protein ubiquitination*. Nat. Biotechnol. 21, 921-926.

Peng, J., M.J. Kim, et al. (2004) *Semiquantitative proteomic analysis of rat forebrain postsynaptic density fractions by mass spectrometry*. J. Biol. Chem. 279, 21003-21011.

Porter, V.R., W. Buxton, et al. (2003) *Frequency and characteristics of anxiety among patients with Alzheimer's disease and related dementias*. J. Neuropsychiatry Clin. Neurosci. 15, 180-186.

Puls, A., S. Schmidt, F. Grawe & S. Stabel (1997) *Interation of protein kinase C zeta with ZIP, a novel protein kinase C-binding protein*. Proc. Natl. Acad. Sci. USA 94, 6191-6196.

Rankin, C.A., Q. Sun, & T.C. Gamblin, (2005) *Pseudo-phosphorylation of tau at Ser202 and Thr205 affects tau filament formation*. Brain Res. Mol. Brain Res. [epub ahead of print].

Robertson, J., J. Curley, J. Kaye, et al. (2005) *apoE insoform and measures of anxiety in probable AD patients and Apo3 mice*. Neurobiol. Aging 26, 637-643.

Sayin, U., T.P. Sutula, & C.E. Staftstrom, (2004) *Seizures in the developing brain cause adverse long-term effects on spatial learning and anxiety*. Epilepsia 45, 1539-1548.

M.L. Seibenhener, J.R. Babu, et al. (2004) *Sequestosome 1/p62 is a polyubiquitin chain binding protein involved in ubiquitin proteasome degradation*. Mol. Cell. Biol. 24, 8055-8068.

Shevchenko, A., M. Wilm, O. Vorm, & M. Mann, (1996) *Mass spectrometric sequencing of proteins silver-stained polyacrylamide gels*. Anal. Chem. 68, 850-858.

Sutherland, R.J., I.Q. Whishaw, J.C. Regehr, (1982) *Cholingergic receptor blockade impairs spatial localization by use of distal cues in the rat*. J. Comp. Physiol. 96, 563-573.

Tanemura, K., M. Murayama, et al. (2002) *Neurodegeneration with tau accumulation in a transgenic mouse expressing V337 M human tau*. J. Neurosci. 22, 133-141.

Wang, Z. & M.C. Figueiredo-Pereira, (2005) *Inhibition of sequestosome 1/p62 up-regulation prevents aggregation of ubiquitinated proteins induced by prostaglandin J2 without reducing its neurotoxicity*. Mol. Cell. Neurosci. 29, 222-231.

Wang, Q., R.L. Woltjer, P.J. Cimino, et al. (2005) *Proteomic analysis of neurofibrillary tangles in Alzheimer disease identifies GAPDH as a detergent-insoluble paired helical filament tau binding protein*. FASEB J. 19, 869-871.

Wenk, G.L., (2003) *Assessment of spacial memory using the radial arm maze and Morris water maze*. Current Protocols In Neuroscience. John Wiley & Sons, Inc., Unit 8.5A.

Xie, J. & Q. Guo, (2005) *PAR-4 is involved in regulation of β-secretase cleavage of the Alzheimer amyloid precursor protein*. J. Biol. Chem. 280, 13824-13832.

* cited by examiner

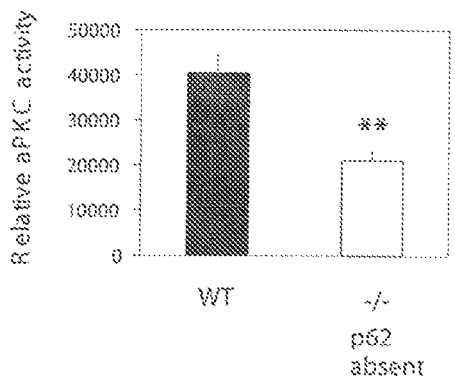
FIG. 2
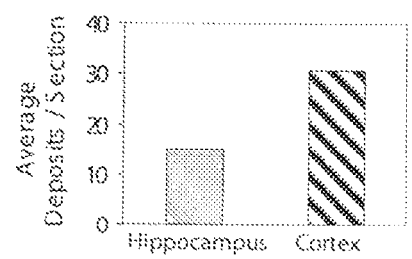
FIG. 3
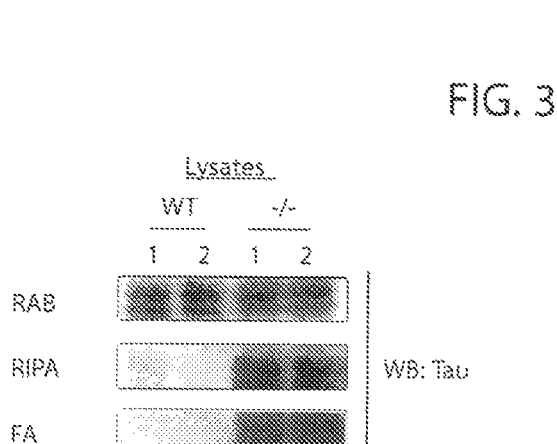
FIG. 4
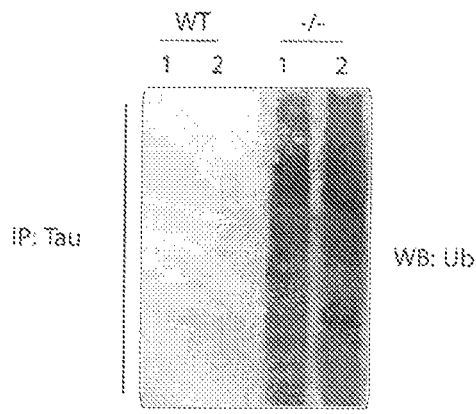

P62 AS A DIAGNOSTIC TOOL FOR ALZHEIMER'S DISEASE

CROSS-REFERENCE TO RELATED APPLICATIONS

This application claims the benefit of U.S. Provisional Application No. 60/723,782 filed Oct. 5, 2005.

STATEMENT REGARDING FEDERALLY SPONSORED RESEARCH OR DEVELOPMENT

This work was supported by a National Institutes of Health-National Institute of Neurological Disorders and Stroke Contract/Grant Number: 2R0/NS033661-07A2.

INCORPORATION-BY-REFERENCE OF MATERIAL SUBMITTED ON A COMPACT DISC

Not Applicable

BACKGROUND AND SUMMARY OF THE INVENTION

The present invention relates to molecular biology in general, with emphasis on proteins affecting the development of metabolic syndrome and related diseases, for example and without limitation, mild cognitive impairment and Alzheimer's Disease.

Metabolic syndrome often refers to a combination of medical disorders that affect a large number of people in a clustered fashion. Metabolic syndrome is generally characterized by a group of metabolic risk factors in one person, including abdominal obesity, atherogenic dyslipidemia (blood fat disorders—high triglycerides, low HDL cholesterol and high LDL cholesterol—that foster plaque buildups in artery walls), elevated blood pressure, insulin resistance, or glucose intolerance, prothrondotic state, and proinflammatory state. Metabolic syndrome is a precursor to many diseases including, but not limited to: mild cognitive impairment, Alzheimer's Disease, Parkinson's Disease, Huntington's Disease, Amyotrophic Sclerosis, corticobasal degeneration, progressive supranuclear palsy, Pick's Disease, and Niemann-Pick's Disease. Oftentimes, the term metabolic syndrome is used to describe the early stages of the diseases listed above and other related diseases.

One of the diseases related to metabolic syndrome, Alzheimer's Disease, affects approximately 4.5 million individuals in the United States, with a projected rise to 14 million individuals by the year 2050. Protein aggregates composed of tau protein and extra cellular plaques of amyloid beta (Aβ) are characteristic pathological features of Alzheimer's Disease affecting the brain and causing behavior changes such as anxiety and loss of synaptic function.

Various risk factors exist and enhance the probability of an individual to develop Alzheimer's Disease. One major factor is age, while another major factor is Type II diabetes. Overeating and obesity are common causes of insulin resistance leading to Type II diabetes. In fact, simply being overweight (i.e., having a body mass index of greater than 25) raises the risk of an individual developing Type II diabetes. Conversely, most individuals with Type II diabetes develop mild cognitive impairment and ultimately Alzheimer's disease. In the past 50 years, there has been a dramatic shift in the rise of Alzheimer's Disease cases. High fat diets have been shown to induce insulin resistance, but less is known about the effects of sugar intake. Alzheimer's Disease may be Type III diabetes.

The p62 protein operates in both receptor mediated activation of kinase cascades and in ubiquitin signaling. P62 serves as a polyubiquitin chain binding protein and is a scaffold for the atypical protein kinase C (aPKC). P62 also serves to traffic proteins to a structure known as an aggresome which is a region of a cell where proteins are sorted and routed to other cellular compartments. The sequestration of aggregates in the aggresome protects cells that are dependent upon the ability of the p62 protein to bind polyubiquinated proteins through its C terminal ubiquitin associated domain. Conversely, the N-terminus of the p62 protein interacts with a proteasome, which is a large protein complex that degrades proteins tagged for elimination, particularly those tagged with ubiquitin. Accordingly, p62 plays a role in protein degradation by shuttling proteins from a sorting compartment, the aggresome, to the degradation department, the proteasome. Alternatively, p62 may also transport polyubiquitinated proteins for degradation by the autophagosome. Protein p62 also interacts with members of the Trk transmembrane protein family, and an absence in p62 impairs Trk internalization and signaling.

The TrkB family of transmembrane proteins serves as receptors for neurotrophic factors. Specific mutations in TrkB have been linked to regulation of food intake, body weight control, obesity and insulin resistance. Mutations in the TrkB transmembrane protein, as well as brain-derived neurotrophic factor, have been linked to Alzheimer's Disease. Geetha and Wooten have demonstrated that TrkB exerts its physiological effects through association with signal scaffolds, such as the p62 protein, J. Biol. Chem. 278 (7): 4730-4739.

It was surprisingly found that the p62 protein has a profound effect on the pathways that cause hyperphosphorylation and polyubiquination of tau proteins, and deposits of APP/amyloid beta. The hyperphosphorylation of tau and its accumulation is coincident with development of insulin resistance. Thus, disturbances in p62 protein expression lead to metabolic syndrome, Alzheimer's Disease and may be a contributing factor to development of other neurodegenerative diseases.

By detecting the absence of p62 protein, a method for screening a mammal for metabolic syndrome or related diseases is established. Since the p62 protein is intricately involved in the accumulation of tau protein and amyloid beta protein, and is also involved in creating insulin resistance in mammals, p62 is a metabolic marker for cognitive decline, and the detection of the presence/absence/concentration of p62 in mammalian tissues provides a mechanism for the early detection of neurological diseases, such as Alzheimer's Disease and various other related neurological diseases. The detection of the absence of p62 protein can be accomplished by supplying a tissue sample, extracting proteins from the tissue sample, and analyzing the extracted proteins to determine whether p62 is present or absent. It is contemplated that this type of detection will diagnose a predisposition for metabolic syndrome, Alzheimer's Disease, Parkinson's Disease, Huntington's Disease, Amyotrophic Lateral Sclerosis, corticobasal degeneration, progressive supranuclear palsy, Pick's Disease, and/or Niemann-Pick's Disease.

A method for screening a mammal for metabolic syndromes comprising the steps of detecting the level of p62 protein in a metabolic pathway, and determining whether the level of p62 protein in the metabolic pathway is below a threshold level is also contemplated. This method further includes obtaining a tissue sample, extracting proteins from the tissue sample and analyzing the extracted proteins to determine the concentration of the p62 protein within the sample. Alternatively, if tissue sample is limiting, p62 levels can be detected using Quantitative PCR (QPCR) techniques.

A pharmaceutical composition for therapeutic supplementation of a metabolic pathway is also contemplated. The composition comprises p62 protein or an amide, ester or salt thereof and a pharmaceutically effective carrier. Such pharmaceutical composition would have an inhibitory action on phosphorylation of tau protein and extracellular plaques of amyloid beta and would also operate to lower blood insulin levels and may alter feeding behavior.

BRIEF DESCRIPTION OF THE SEVERAL VIEWS OF THE DRAWINGS

FIG. 2 is a bar graph demonstrating relative atypical protein kinase C activity in mice lacking the ability to produce the p62 protein versus wild-type mice.

FIG. 3 is a bar graph demonstrating the average deposits per section of amyloid beta plaques in the hippocampus and cortex of mouse brains lacking the ability to produce the p62 protein.

FIG. 4 is a western blot analysis demonstrating a hyperexpression of the tau protein and ubiquitin in protein fractions isolated from mice unable to produce the p62 protein versus wild-type mice.

DETAILED DESCRIPTION OF THE INVENTION

Metabolic syndrome is a metabolic disease and is a precursor to many diseases, particularly mild cognitive impairment and Alzheimer's Disease. Neurofibulary tangles of hyperphosphorylated tau protein that progressively accumulate is a neuropathological hallmark of Alzheimer's Disease. In addition, plaques composed of aggregated amyloid beta protein are also present and are believed to be a pathogen and characteristic of Alzheimer's Disease. Moreover, the regulation of insulin levels in the blood has a significant effect on the development of insulin resistance, tau phosphorylation and also on the accumulation of amyloid beta. It has been surprisingly determined that the regulation of tau protein, amyloid beta protein and insulin levels are directly affected by the p62 protein. Accordingly, detection and analysis of the presence or levels of p62 in mammalian tissues will function as a risk determinant for the development of metabolic diseases such as metabolic syndrome and as a risk determinant for further development of neurological diseases such as Alzheimer's Disease, Parkinson's Disease, Huntington's Disease, Amyotrophic Lateral Sclerosis, corticobasal degeneration, progressive supranuclear palsy, Pick's Disease, and Niemann-Pick's Disease.

Figure 1:
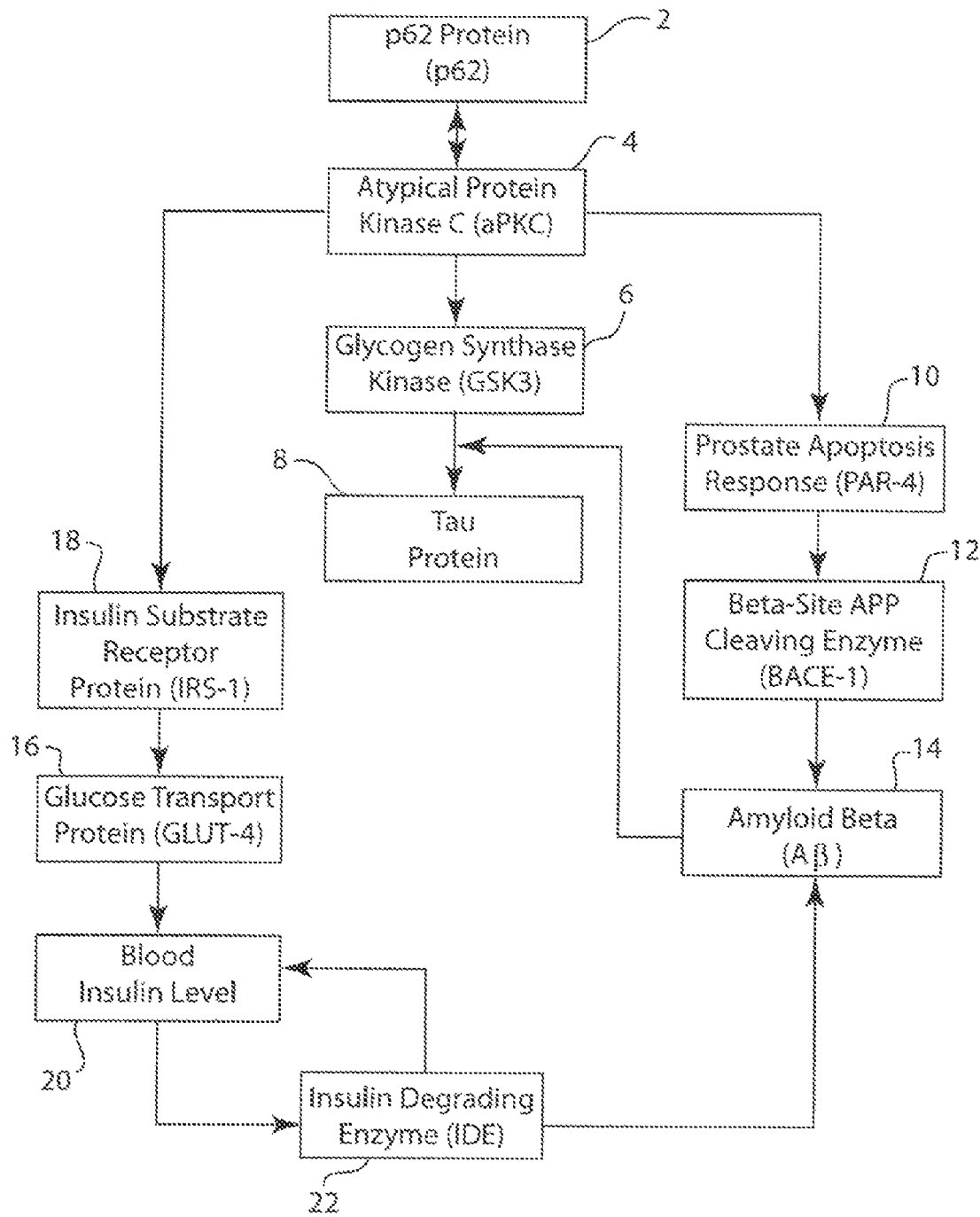
FIG. 1 is a flow chart demonstrating the effect that the p62 protein has on certain metabolic pathways.

Referring now to FIG. 1, the p62 protein (2) is a binding partner for atypical protein kinase C (aPKC) (4). Reduction or elimination of p62 protein levels decreases the levels of atypical protein kinase C. The partnership between the p62 protein (2) and the atypical protein kinase C (4) further affects several metabolic pathways. First, when p62 protein (2) is reduced or eliminated, it does not bind with atypical protein kinase C (4), and there is a reduction in glycogen synthase kinase 3 (GSK 3) (6) levels. Glycogen synthase kinase 3 (6) is a serene/threonine protein kinase that is highly expressed in the central and peripheral nervous system. Glycogen synthase kinase 3 (6) phosphorylates several substrates, including the tau protein (8). Glycogen synthase kinase 3 (6) phosphorylates the microtubule associated protein tau (8) in neurons. Hyperphosphorylated protein tau (8) has a lower affinity for microtubules and accumulates as paired helical filaments, which is a main component constituting neurofibulary tangles and neuropil threads in the brains of mammals affected with Alzheimer's Disease. The neurofibulary tangles and neuropil threads cause depolymerization of microtubules, leading to the death of axons and neuritic dystrophy. Neurofibulary tangles are consistently found in diseases such as Alzheimer's Disease, Amyotrophic Lateral Sclerosis, corticobasal degeneration, Parkinson's Disease, Huntington's Disease, progressive supranuclear palsy, Pick's Disease, and Niemann-Pick's Disease. Thus, reduction or elimination of p62 protein levels causes an increase in glycogen synthase kinase 3 levels, which causes a hyperphosphorylation of the tau protein (8). This hyperphosphorylation of the tau protein (8) results in accumulation of the tau protein as neurofibulary tangles and is a hallmark of Alzheimer's Disease and other dementias. Thus, detection of the presence or absence of the p62 protein in mammalian tissues can provide a screening mechanism for various neurodegenerative diseases.

Figure 5:
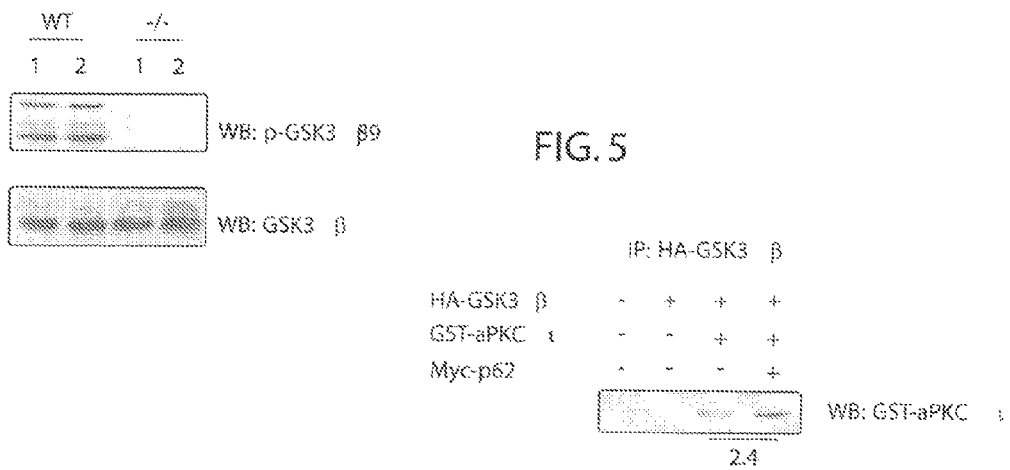
FIG. 5 demonstrates the results of a western blot analysis to detect the presence of glycogen synthase kinase 3 (GSK3β) in mice incapable of producing p62 versus wild-type mice.

To fully explore the mechanisms detailed in FIG. 1, tissue samples were immunoblotted with a glycogen synthase kinase 3 antibody recognizing phosphorylated and non-phosphorylated glycogen synthase kinase 3, see, FIG. 5. The inventors found that in mice that did not express the p62 protein, there was constitutive activation of the glycogen synthase kinase 3 through phosphorylization. Similar tests were performed with respect to atypical protein kinase C activity. Tissue samples from mice that were incapable of producing the p62 protein ($^{-/-}$) were observed to exhibit a significant reduction in atypical protein kinase C activity compared to wild-type (WT) mice, see, FIG. 2. Thus, the inventors surprisingly found that the interaction between glycogen synthase kinase 3 and atypical protein kinase C was enhanced two-fold in the presence of p62, resulting in a parallel two-fold increase in glycogen synthase kinase 3 phosphorylation.

Since p62 has such an effect on tau hyperphosphorylation, a method for screening a mammal comprising the step of detecting the absence of p62 protein is a strong determinant as to whether the mammal will develop a neurological metabolic disease, such as Alzheimer's Disease, Parkinson's Disease, Huntington's Disease, Amyotrophic Lateral Sclerosis, corticobasal degeneration, progressive supranuclear palsy, Pick's Disease, and/or Niemann-Pick's Disease. In performing such an analysis, a tissue sample is obtained and proteins are extracted from the tissue sample, using known methods, as further described herein. The extracted protein is then analyzed to determine whether the p62 protein is present or absent by any one of various methods known in the art, including, but not limited to those described herein. Alternatively, the extraction proteins may be analyzed to determine whether the level of p62 protein in the metabolic pathway is below a threshold level of fifty percent compared to normal p62 levels.

Antibodies to p62 protein are well known, see, U.S. Pat. No. 5,610,276. Using such antibodies, proteins extracted from tissue samples may be separated by 10% SDS-page and immunoblotted with the anti-p62 antibody. Other methods for checking the presence or absence of p62 proteins and/or detecting the concentration of p62 proteins are well known in the art and are deemed to be within the scope of the present disclosure.

Figure 9:
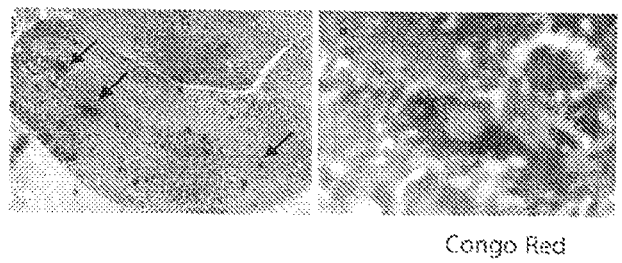
FIG. 9 are photomicrographs of the hippocampus and cortex of mouse brains incapable of producing p62 protein stained with an antibody that detects amyloid beta.

Referring back to FIG. 1, the p62 protein (2) also has an effect on the accumulation of amyloid beta (Aβ) plaques. Prostate apoptosis response-4 (PAR-4) protein (10) interacts with atypical protein kinase C (4). Reduced levels of atypical protein kinase C decreases prostate apoptosis response-4 protein levels. The prostate apoptosis response-4 protein (10) interacts with beta-site APP cleaving enzyme (BACE-1) (12). A decrease in the activity of the prostate apoptosis response-4 protein decreases beta-site APP cleaving enzyme activity. This decrease in beta-site APP cleaving enzyme activity enhances amyloid beta protein (14) production. This enhanced production of amyloid beta (14) has two profound physiological effects: first, it causes further hyperphosphorylation of the tau protein (8) leading to the accumulation of tau protein as neurofibulary tangles; and second, amyloid beta (14) causes intraneural accumulation and extracellular protein plaques on neurological tissue and neurons. FIGS. 3 and 9 demonstrate that in serial sections from mice incapable of producing the p62 protein and stained with 4G8 antibody, an antibody specific for amyloid beta, the presence of numerous plaques in both the hippocampus and cortex are revealed. Accordingly, the absence of p62 leads to tau hyperphosphorylation, neurofibulary tangles of specific confirmations accompanied by accumulation of amyloid beta and neurodegradation.

Thus, a method for screening that includes the step of detecting the absence of p62 protein is a powerful screening test because p62 lies in a pathway that controls accumulation of hyperphosphorylated polyubiquinated tau protein and amyloid beta. P62 is the first protein where reduced expression has been shown to cause neurodegradation along with pathology specific to Alzheimer's Disease. Therefore, as aforementioned, a method for screening a mammal for metabolic diseases comprising the step of detecting the absence of p62 protein by extracting proteins from a tissue sample and analyzing the extracted protein to determine either the presence of absence of p62 or the concentration of p62 is an effective screening for various neurological metabolic diseases, including Alzheimer's Disease, Parkinson's Disease, Huntington's Disease, Amyotrophic Lateral Sclerosis, corticobasal degeneration, progressive supranuclear palsy, Pick's Disease, and Niemann-Pick's Disease.

Referring again to FIG. 1, a reduction/elimination of p62 protein (2) levels and, therefore, a reduction in p62 protein (2) and atypical protein kinase C (4) interaction is a primary contributor to insulin resistance and to the production of amyloid beta (14), as well as hyperphosphorylation of tau protein (8). The primary contributor to insulin resistance is a decrease in insulin-stimulated glucose transport activity protein (GLUT4) (16). P62 protein interaction with the atypical protein kinase C may affect the activity of the insulin receptor substrate proteins (IRS-1 and 2)(18) either directly or indirectly. Thus, a decrease in p62 levels may decrease the activity of the atypical protein kinase C, and in turn result in the reduction in the activity or phosphorylation of IRS1 or 2. The insulin substrate receptor protein (18), when phosphorylated, affects the translocation of insulin stimulated glucose transport protein (GLUT-4) (16) across cell membranes. A decrease in insulin receptor substrate protein production impairs glucose transfer protein translocation across cell membranes. Impaired glucose transfer protein translocation across cell membranes increases insulin levels (20) and is a contributor to cellular insulin resistance. This increase in the blood insulin level competes for and blocks the activity of insulin degrading enzyme (IDE) (22) which contributes to the formation of amyloid beta (14). As aforementioned, amyloid beta (14) can serve as a tau kinase, or insulin itself can activate tau kinases, leading to aberrant phosphorylation and aggregation of tau protein (8). Thus, the ability to screen individuals for the presence, absence or concentration of p62 protein in neurological tissues, blood, liver, pancreas and/or skeletal muscle tissues is important in addressing the risk of such mammal to many metabolic diseases. Screening mammals for p62, therefore, can not only be effective screening for Alzheimer's disease, but also other neurological diseases.

As p62 levels decline, the first physical manifestation of that decline is anxiety followed by loss of short term memory. Symptoms of anxiety in humans are varied and include: intense worry and feelings of dread, poor concentration and restlessness, irritability and poor sleep, muscle tension and trembling, palpitations or chest pains, profuse sweating and hot flashes. As memory and thinking skills fade, a person with Alzheimer's Disease is challenged by everyday situations and demands. Changes in a person's surroundings, lack of social contact with others, and lack of routine can all compound anxiety in a person developing Alzheimer's Disease. Moreover, changes in anxiety precede insulin resistance and development of cognitive decline. Therefore, in humans, an initial screening of individuals displaying anxiety, along with metabolic profiles of p62 presence/absence/concentration would provide an early temporal indication that such an individual is likely to develop Alzheimer's Disease, or possibly other related neurological diseases. Accordingly, individuals who both display no or low p62 levels and also who display anxiety, are prime candidates for therapeutic supplementation of p62 protein.

Figure 12:
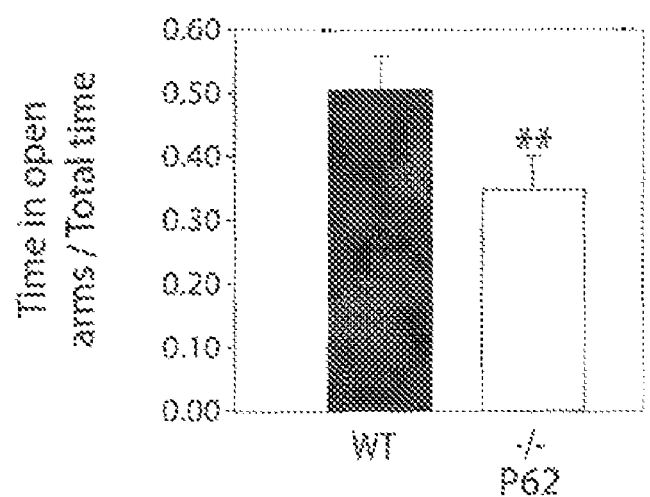
FIG. 12 is a bar graph demonstrating that wild-type mice spent more time exploring open arms of an eight arm radial maze than p62$^{-/-}$ mice, indicating anxiety in the p62$^{-/-}$ mice.

Behavioral tests were performed on wild-type and p62$^{-/-}$ mice to establish the early temporal relationship between p62 protein and anxiety. A probe trial consisting of a 60 second free swim was used to test the spatial knowledge of the location of a visible platform and location search strategies employed by the mice relative to external cues. On the probe trial, p62$^{-/-}$ mice exhibited clear evidence for deficits in spatial learning. A stringent measure of spatial navigation is to examine time spent in the inner, middle and outer zones of a Morris water maze (San Diego Instruments, San Diego, Calif., USA). The p62$^{-/-}$ mice spent significantly more time in the outer zone along the wall of the tank and significantly less time in the inner zone, indicative of thigmotaxia, i.e., wall hugging. To further examine spatial learning, mice were tested in an 8 arm radial maze. Upon opening doors in the maze, wild-type mice entered individual arms of the maze quickly to obtain all food rewards. By comparison, the p62$^{-/-}$ mice spent a significant amount of time in the central chamber of the maze prior to their first, if any, arm entry. In most cases, the p62$^{-/-}$ mice did not complete the maze. The tendency of the p62$^{-/-}$ mice to remain stationary in the maze and their avoidance of exploratory behavior is a reflection of anxiety. Accordingly, the inventors employed the time of first arm entry as a measure of anxiety-like behavior, see, FIG. 12. An assessment of the data in FIG. 12 revealed that p62$^{-/-}$ mice were significantly less likely to explore the maze environment. This suggests that there is an association between loss or lowering of p62 protein and anxiety.

To examine this behavior in greater detail, the mice were tested in an elevated plus maze and in an open field maze, techniques that are known in the art as standard ways to measure anxiety. Both tests revealed a significantly higher level of anxiety behavior in the p62$^{-/-}$ mice compared to the wild-type mice.

Finally, it has been discovered that the absence of p62 protein causes a disregulation of TrkB signals. Accordingly, p62 serves to integrate TrkB, causing obesity and insulin resistance. Moreover, overexpression of p62 may restore normal food consumption and TrkB signaling, restore insulin sensitivity and enhance cognitive abilities, thereby delaying progression of neurological diseases.

Accordingly, a pharmaceutical composition for therapeutic supplementation of a metabolic pathway will be effective to accomplish these goals. The pharmaceutical compensation may comprise p62 protein or an amide, ester or salt thereof, and a pharmaceutically effective carrier. Pharmaceutical effective carriers include any and all solvents, dispersion media, coatings, antibacterial and antifungal agents, isotonic and absorption delaying agents, and the like, compatible with pharmaceutical administration. The use of media agents for pharmaceutically active substances is well known in the art. The sequence coding for the p62 polypeptide and related polypeptides are disclosed in U.S. Pat. No. 6,291,645, and the subject matter of that patent is incorporated herein by reference.

The subject matter of the present application is further illustrated by the following examples which in no way should be construed as being further limiting. The contents of all cited references and patents cited throughout this application are hereby expressly incorporated by reference.

EXAMPLES

The following materials and methods were used throughout examples:

Generation of P62$^{-/-}$ Mice

Knock out mice (p62$^{-/-}$) were generated as described previously (Duran et al. Dev. Cell 6, 303-309, 2004). For the duration of the study all mice were housed in a pathogen-free barrier environment. We intercrossed p62$^{+/+}$ and p62$^{-/-}$ mice to obtain an isogenic mouse strain. The genotypes of the offspring were verified by PCR with allele specific primers. For p62$^{+/+}$ we used forward primer (5'-GGG GGC TAC TAC CGG GGA CAT TAT-3') [SEQ ID NO 2] and reverse primer (5'-CGA CCC CAC TGC CTA CTC TTT TCT-3') [SEQ ID NO 3], while p62$^{-/-}$ was detected with the forward primer (5'-GGG GGC TAC TAC CGG GGA CAT TAT-3') [SEQ ID NO 4] and reverse primer (5'-CTT GGG TGG AGA GGC TAT TC 3') [SEQ ID NO 5]. All animals employed in the studies were six months of age and handled according to the Auburn University IACUC which abides by NIH guidelines.

Human Brain Tissue Samples

Cortical brain homogenates were isolated from individuals having Alzheimer's Disease. Cortical brain homogenates were also isolated from individuals not having Alzheimer's Disease as a control.

Isolation of Soluble And Insoluble Fractions

Soluble and insoluble protein fractions were prepared as described (Dou et al. Proc. Natl. Acad. Sci. USA 2, 721-726, 2003). Briefly, the brain sample was homogenized in 1 ml/gm of ice-cold 1 M sucrose in RAB buffer, pH 7.0 (0.1 M MES, 1 mM EGTA, 0.5 mM MgSO$_4$, 0.75 M NaCl, 0.02 M NaF, 1 mM PMSF, 0.1% protease inhibitors). The homogenate was centrifuged at 50,000×g for 20 min at 4° C. The pellet was extracted with 1 ml/gm tissue in RIPA buffer (50 mM Tris pH 8.0, 150 mM NaCl, 1% Nonidet P-40, 5 mM EDTA, 0.5% sodium deoxycholate, 0.1% SDS) and centrifuged at 50,000×g for 20 min at 4° C. to obtain RIPA soluble fractions. The pellet was sonicated with 70% formic acid and lyophilized to yield the highly insoluble fraction. Protein on all 3 fractions (RAB, RIPA, FA) was determined using the DC protein assay (Bio-Rad Laboratories, Hercules, Calif., USA) and an equal concentration, of each were electrophoresed and Western blotted, according to conventional techniques.

Transfection, Immunoprecipitation and Western Blot Analysis

Transfection of human embryonic kidney (HEK) cells, immunoprecipitation and Western blotting were conducted as previously described (Baba et al., J. Neurochem. 94, 192-203, 2005). Hemagglutinin (HA)-tagged GSK3β was obtained from Dr. James Woodgett (Ontario Cancer Institute, Toronto, Ontario, Canada). We employed mouse anti-ubiquitin (Santa Cruz Biotechnology, Santa Cruz, Calif., USA), rabbit anti-GSK3 and anti-GSK3 α/β (Ser 9/21) (Cell Signaling Technology Inc., Beverly, Mass., USA). Measure of aPKC$_t$ activity was conducted with antibody from Santa Cruz Biotechnology (Santa Cruz, Calif., USA) using myelin basic protein as substrate. For Western blotting of the human cortical brain homogenates, actin is used as an internal sample for sample variance.

Reverse Transcriptase (RT)-PCR and Real-Time Quantitative PCR

Dissected cortical grey matter is cut into small pieces in the frozen state and approximately 70 mg is homogenized immediately in RNA-Bee (Iso-Tex Diagnostics, Friendswood, Tex., USA) solution and RNA was isolated. Alternatively, blood may be collected and RNA may be isolated from the blood in the same manner. RNA that is intact by electrophoresis and has a $A_{260}/A_{280}$ ratio $\geq 1.9$ is used for cDNA synthesis. The RT-PCR system (RETRO script kit) is available from Ambion, Inc. of Austin, Tex., USA. 2 μg total RNA is mixed with 2 μl Oligo (dT) and nuclease-free water. The mixture is centrifuged briefly and heated 3 min at 70-85° C. to denature the RNA secondary structure. The tubes are placed on ice, centrifuged briefly, and remain on ice for at least 1 min. RT components (2 μl 10×RT buffer, 4 μl dNTP mix, μl RNase inhibitor and 1 μl Reverse Transcriptase) are added, mix gently, spun briefly and incubated at 42° C. for 1 h. Then, reaction is incubated at 92° C. for 10 min to inactivate the Reverse Transcriptase. All cDNA samples can be stored at −20° C. until use.

Relative quantitative real-time PCR may be performed to quantify p62 mRNA level at this time. The cDNA product is used to perform real-time PCR with power SYBR Green Mix kit available from Applied Biosystems of Foster City, Calif., USA. All reactions are performed in a 25 µl mixture containing 1×SYBR, 0.5 µM primers mix (forward and backward) and cDNA. Primers are generally 18-25 bp long with Tms around 60° C. For p62, the forward primer 5'-ACG GCA GAA TCA GCT TCT GGT C-3' [SEQ ID NO 6] binds at bp 701 and the reverse primer 5'-TCA ATG CCC AGA GGG CTA AG-3' [SEQ ID NO 7] binds at bp 801 of the cDNA. The forward primer for endogenous reference gene β-actin, 5'-ACT GGC ATC GTG ATG GAC TC-3' [SEQ ID NO 8], binds at bp 529 of the full-length cDNA. The reverse primer sequence, 5'- TCA GGC AGC TCG TAG CTC TT-3' [SEQ ID NO 9], binds at position 815.

Thermo cycling is subsequently performed in Applied Biosystems 7500 real-time PCR machine. Upon completion of the amplification program, a melt curve is generated for the samples as well as agarose gel electrophoresis to confirm product formation and purity. The ratio of p62 to actin PCR products in control samples is compared with those obtained from those with dementia to confirm the probability of neurodegenerative disease. Those samples with less than 50% p62 expression are likely to develop AD or other neurodegenerative diseases.

Polyubiquitin Chain Analysis

Heavy-isotope labeled internal peptides corresponding to all seven types of human polyubiquitin linkages were synthesized and quantified by amino acid analysis (Cell Signaling Technology, Inc., Beverly, Mass. USA), including di-glycine tagged signature peptides at Lys6, Lys1, Lys27, Lys29, Lys33, Lys48 and Lys63 (Peng J et al., Nat. Biotechnol. 21, 921-926, 2004). The synthetic peptides were used to optimize the selection of precursor ions and parent ions, and to establish fragmentation conditions in a selective reaction monitoring (SRM) on an LCQ-DECA XP ion trap mass spectrometer (Thermo Finnigan, San Jose, Calif., USA). The quantification of the linkage was carried out essentially as previously described (Gerber SA et al., Proc. Natl. Acad. Sci. USA, 100, 6940-6945, 2003; Peng J et al. 2004, supra). Immunoprecipitated protein samples (50%) were separated on 10% SDS gel and stained with Coomassie Blue G-250. Proteins larger than the immunoglobulin G heavy chain (~55 kDa) were excised from the gel and subjected to in-gel digestion. A mixture of seven isotopically labeled signature peptides (1 pmole of each) was added to the in-gel digestion solution prior to incubation. After proteolysis, a peptide mixture containing the endogenous peptides and internal standards was separated by reverse-phase chromatography. An endogenous peptide was eluted at the same retention time as the heavy labeled internal standard. Both peptides were selected, fragmented and analyzed in a selective reaction monitoring mode. The ratio between the intensities of the fragment ion pairs allowed an accurate measure of the relative abundance of the endogenous peptide versus the internal standard of known quantity. All seven linkages were quantified simultaneously in the same run. About 5-20% of each sample was used for each mass spectrometric analysis. Each sample was quantified three times to obtain the relative standard deviation (RSD).

Pathology And Immunohistochemistry

Mouse brains were dissected and drop fixed in 4% paraformaldehyde in 0.1 M phosphate buffer pH 7.4. Each brain was processed, embedded in paraffin and 5 µm sections cut for all the immunohistochemical staining. Parallel sections from 3 mice each were stained with hematoxylin-eosin, Gallyas silver stain (Gallyas, 1971) and thioflavin-S. For plaque staining, we used purified mouse 4G8 antibody (Signet Laboratories Inc., Dedham, Mass., USA), which recognizes Aβ. To detect tangles rabbit anti-neurofibrillary tangle antibody was employed (Chemicon International, Temecula, Calif., USA). Slides were processed employing the vector M.O.M immunodetection kit (Vector Laboratories Inc., Burlingame, Calif., USA). For the plaque staining, the sections were incubated in 70% formic acid at room temperature (RT; 22.25° C.) for antigen retrieval. Antibodies to phosphorylated tau (PHF-1 (Ser 396/Ser 404) and CP-13 (Ser 202)) and to abnormal tau conformation (MC-1 (conformational ALZ 50)) were a generous gift from Dr. Peter Davies (Albert Einstein College of Medicine, Bronx, N.Y.). For MC-1 and CP-13 staining, we used the Histostain-DS kit (Zymed Laboratories, South San Francisco, Calif., USA); for PHF-1, the Histomouse-MX kit was employed (Zymed Laboratories). For counting, including estimates of the flame shaped neurofibrillary tangles, loss of neurons (between CA1 and CA-2) and apoptotic neurons, twelve representative fields of a single section were counted using the 20× objective and averaged. With the configuration of the microscope (per viewing field size) counts were converted and expressed per $mm^2$. Four matched sections of wild-type and $p62^{-/-}$ obtained from 4 animals were stained. The in situ cell death detection kit, POD (Roche Applied Sciences, Indianapolis, Ind., USA) was used to detect apoptotic neurons as described previously (Gotz et al., Science 293, 1491-1495, 2001).

Behavior Testing And Statistical Analysis

Spatial and nonspatial learning was assessed using a Morris water maze (San Diego Instruments, San Diego, Calif., USA). Mice were tested daily over a period of 20 days. During the first 6 days, mice were trained using a visible platform. Training consisted of 4 trials per day at 15 minute intervals for the next 10 days the platform was hidden and stationary across trials. The probe trial consisted of a 60 second free swim performed on day 16 and was used to test spatial knowledge of the location of the platform and location search strategies employed by the mice relative to external cues. For the last 4 days, the platform remained hidden, but was relocated during reverse learning. The start position of the mice, as well as the location of the platform, was randomized across the trials. The SMART (version 2.0.15) computerized animal tracking system (PanLab, Inc., Barcelona, Spain) was used to record pathlength, latency and swim speed of each mouse during the testing periods.

A radial arm maze (RAM) (San Diego Instruments, San Diego, Calif., USA) was used to access spatial learning and memory. Measurements of locomotor activity, as well as any anxiety-related behavior, were performed simultaneously using a multiple unit open-field maze consisting of four activity chambers (San Diego Instruments, San Diego, Calif., USA). Total ambulatory distance, defecation and urination were recorded for each animal.

An elevated plus maze (Colbourne Instruments, Allentown, Pa., USA) was used to measure anxiety-like behavior. The number of open and closed arm entries, time spent in both types of arms, total distance traveled in each arm and total distance traveled were measured.

All behavioral data were subjected to unpaired two-tailed Student's t-tests for between group analyses. All date are represented as mean +/− SEM.

RESULTS

Absence of p62 leads to accumulation of hyperphosphorylated polyubiquinated tau protein along with activation through phosphorylization of GSK3β. As demonstrated in FIG. 4, fifty micrograms of protein extracted from the RAB, RIPA and PA fractions of wild-type or p62$^{-/-}$ mice were separated by 10% SDS-PAGE and immunoblotted with anti-tau or phospho-tau antibody (CP-13/S202). Alternatively, the FA fraction (600 µg) was resuspended in RIPA and immunoprecipitated (IP) with anti-tau and separated by 7.5% SDS-PAGE and immunoblotted with ubiquitin. The absence of the p62 protein demonstrates increased tau and ubiquitin accumulation.

A brain homogenate (50 µg) was immunoblotted with phospho-S9/21 GSK3 antibody and the blot was stripped and reprobed with nonphospho-GSK31β antibody in FIG. 5. The results demonstrate that the absence of p62 resulting in constitutive activation of GSK3β.

Previously discussed FIG. 2 demonstrates activity of aPKS$_1$ measured in two individual brain homogenates (750 µg) by immunecomplex kinase assay. The relative activity was determined by scan of γ-$^{32}$P-ATP incorporated into myelin basic protein (MBP). Atypical- PKC$_t$ activity was significantly reduced in p62$^{-/-}$ compared to wild-type (**P<0.05).

Figure 6:
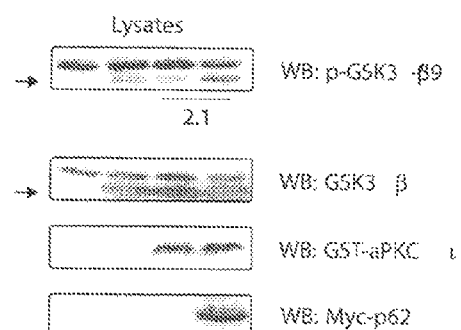
FIG. 6 demonstrates a series of western blot results for transfected cells and demonstrate that the interaction between GSK3β and aPKC$_t$ is enhanced by a factor of 2 in the presence of the p62 protein.

As demonstrated in FIG. 6, HEK cells were transfected with HA-GSK3β, GST-aPKC$_t$ and myc-p62. GSK3β was immunoprecipitated by anti-HA and aPKC$_t$ and blotted with GST. Lysates (50 µg) were blotted with phospho-Ser9 GSK3 and non-phospho GSK3, HA, GST and myc antibodies as shown. The blots were scanned with a computer-interfaced densitometer and the relative fold differences are shown. The interaction between GSK3β and aPKC$_t$ was enhanced by a factor of 2 in the presence of the p62 protein.

Figure 7:
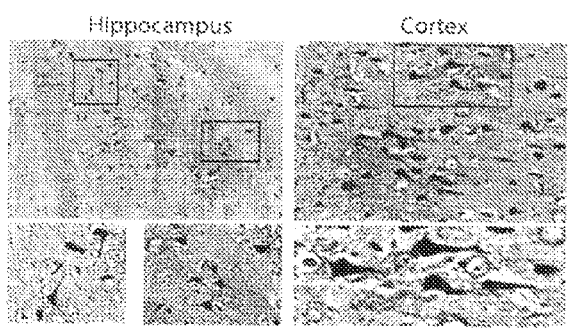
FIG. 7 are photomicrographs of Gallyas silver stained hippocampus and cortex paraffin sectioned mouse brains where the mouse brains are incapable of producing the p62 protein and a bar graph demonstrating quantitative assessment of neurofibulary tangles in such mouse brains.
Figure 7:
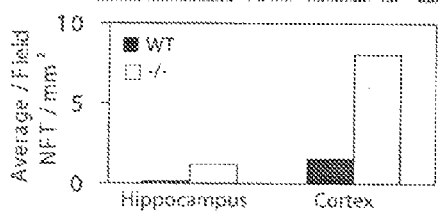

Gallyas silver staining of hippocampus and cortex paraffin-sectioned mouse brains of a p62$^{-/-}$ mouse is shown in FIG. 7. Boxed regions are magnified below. Quantitative assessment of the tangle/flame-shaped neurons in wild-type and p62$^{-/-}$ brain are shown, demonstrating a much higher concentration of neurofibulary tangles in mouse brains incapable of producing the p62 protein.

Figure 8:
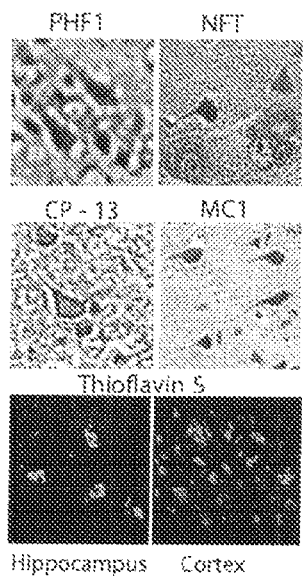
FIG. 8 are photomicrographs of paraffin sections of a mouse brain incapable of producing the p62 protein and stained with antibodies specific for various factors demonstrating neurofibulary tangles.

Paraffin sections of p62$^{-/-}$ mouse brain were immunohistostained with antibody specific for PHF1, NFT, Cp-13, MC1, or thioflavin-S stained. FIG. 8 shows that in mouse brains incapable of providing p62, a much higher concentration of neurofibulary tangles exists.

FIG. 9 demonstrates low (left panel) and high magnification (right panel) of hippocampus and cortex of p62$^{-/-}$ sections immunohistostained with 4G8 antibody, detecting Aβ. The arrows indicate Aβ deposition in the hippocampus section. The graph of FIG. 3 shows the number of plaques per section in hippocampus and cortex of FIG. 9. Thus, the absence of p62 reveals numerous Aβ plaques in both the hippocampus and cortex of mouse brains incapable of producing p62 protein.

Figure 10:
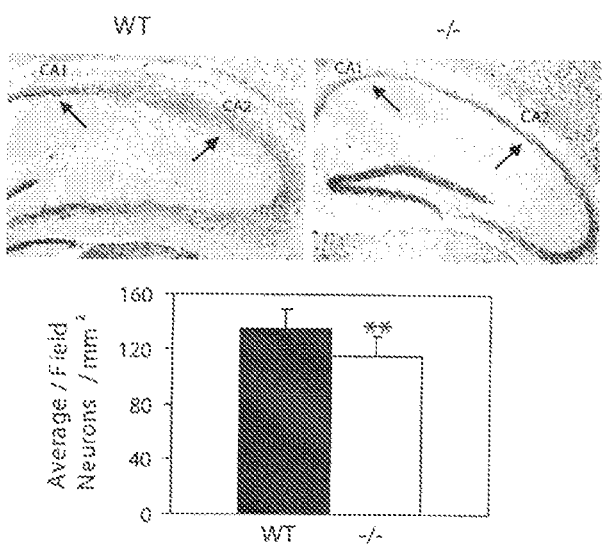
FIG. 10 is a photomicrograph comparing paraffin sections from wild-type mice versus mice incapable of producing p62 protein stained to demonstrate the amount of neurons affected in both samples and including a graph quantifying the average neurons per field in millimeters squared.

In FIG. 10, adjacent matched paraffin sections from wild-type and p62$^{-/-}$ knockout brain w re stained with Hematoxylin and Eosin (HE). Note the reduced thickness of CA1/2 pyramidal cell layer indicated between the arrows. The neurons between CA1 and CA2 regions of the hippocampus were counted and plotted. In p62$^{-/-}$ samples, the number of neurons between CA1 and CA2 were significantly (**P<0.01) less than wild-type.

Figure 11:
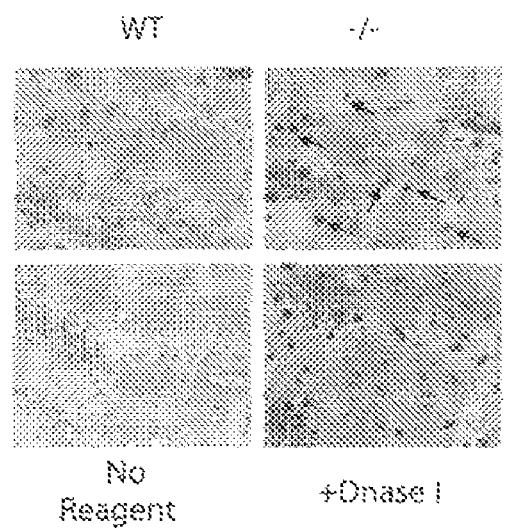
FIG. 11 demonstrates photomicrographs of paraffin sections of mouse brains stained to demonstrate the presence of neurons in wild-type mice versus mice incapable of producing p62 protein.

FIG. 11 demonstrates matched wild-type and p62$^{-/-}$ paraffin sections were stained with TUNEL to detect apoptotic neurons. In the top right panel, p62$^{-/-}$ TUNEL-positive neurons are shown by arrows in cortex region, compared to wild-type. Lower left panel shows the negative control without reagent and positive control in the lower right, pretreated with DNase I. Comparison of wild-type to p62$^{-/-}$ sections reveals an increase of TUNEL-positive neurons in p62$^{-/-}$ mice from 10 per field/mm$^2$ to 127 per field/mm$^2$.

Figure 13:
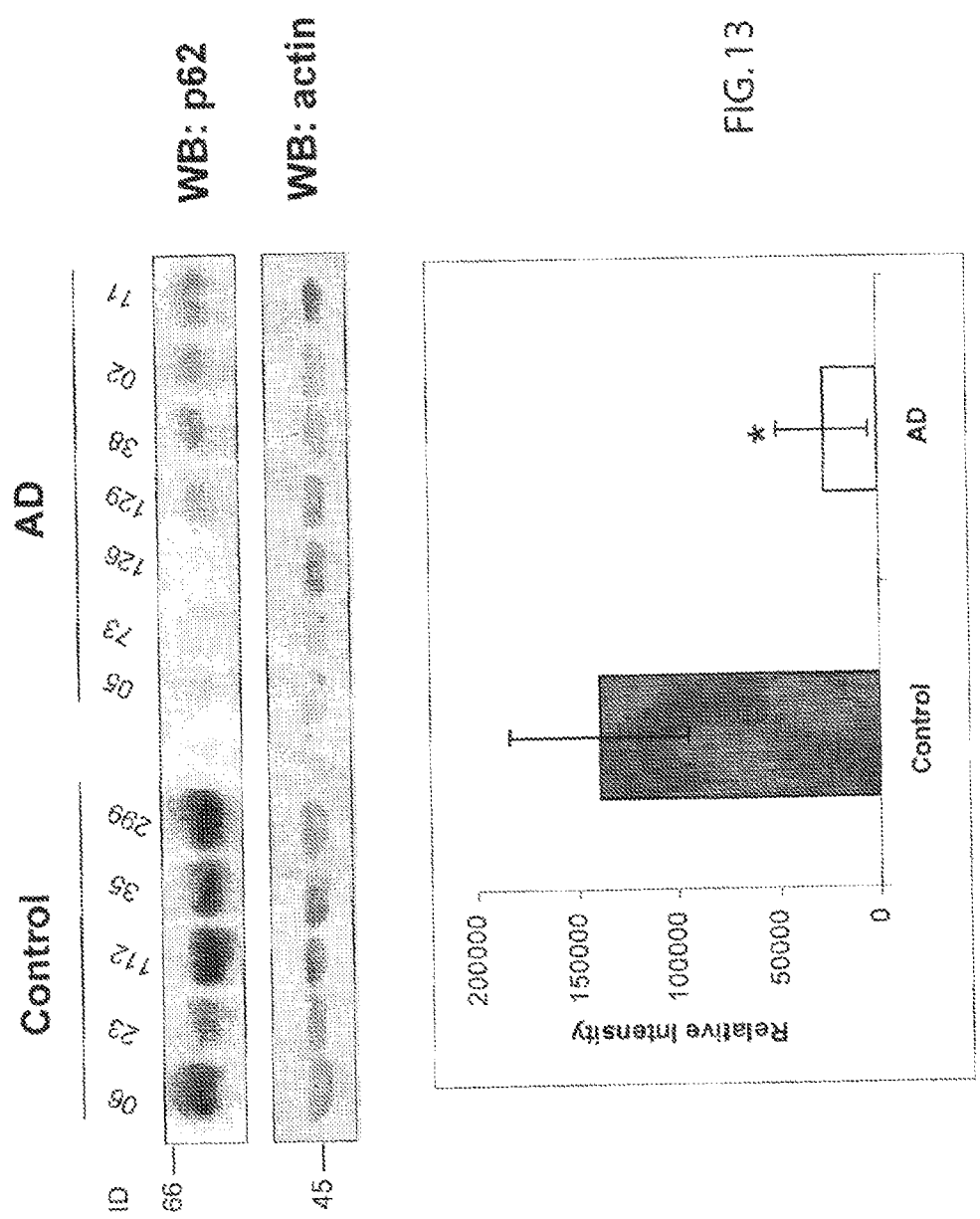
FIG. 13 demonstrates the results of a western blot analysis to detect the presence of p62 protein in control individuals versus individuals having Alzheimer's Disease, and demonstrates the results quantitatively in a bar graph.

As demonstrated in FIG. 13, the expression level of p62 in cortical brain homogenates of Alzheimer's Diseased human brains was compared to control cortical brain homogenates from human brains. Actin was used as an internal sample for sample variance. A comparison of the Alzheimer's Diseased samples to the control samples indicates that the Alzheimer's Diseased samples possess significantly lower levels of p62. The expression of p62 is inversely correlated with the number of neurofibulary tangles in Alzheimer's Diseased brains.

Results regarding the behavioral testing of wild-type and p62$^{-/-}$ mice is discussed in the Detailed Description above.

Those skilled in the art will recognize, or will be able to ascertain using no more than routine experimentation, many equivalents to the specific embodiments of the invention described herein. Such equivalents are intended to be encompassed by the following claims which particularly point out and distinctly claim the subject matter regarded as the invention.

What is claimed is:

1. A method of screening a human for Alzheimer's disease comprising the steps of:
    obtaining a cortical brain tissue sample from a subject;
    measuring the amount of p62 protein in the sample; and
    comparing the measured amount of p62 protein against a control amount of p62 protein from a control brain tissue sample of a non-affected subject;
    wherein Alzheimer's disease is identified when the measured amount of p62 protein is fifty percent or less than the amount of p62 protein in the control sample.

2. The method of claim 1, wherein the brain tissue sample is a cortical brain tissue homogenate.

3. The method of claim 1, wherein the comparing step further comprises:
    obtaining a control brain tissue sample from a subject not affected with Alzheimer's disease; and
    measuring a control amount of p62 protein from the control brain tissue sample.

* * * * *

UNITED STATES PATENT AND TRADEMARK OFFICE
CERTIFICATE OF CORRECTION

PATENT NO. : 7,608,412 B2  
APPLICATION NO. : 11/539035  
DATED : October 27, 2009  
INVENTOR(S) : Marie W. Wooten et al.

Page 1 of 1

It is certified that error appears in the above-identified patent and that said Letters Patent is hereby corrected as shown below:

In The Specification,

Please correct the paragraph following the heading, "STATEMENT REGARDING FEDERALLY SPONSORED RESEARCH OR DEVELOPMENT" in column 1, lines 9-15 to read as follows:

This invention was made with government support under grant number 2RO/NS033661-07A2 awarded by the National Institutes of Health. The government has certain rights in the invention.

Signed and Sealed this  
Fifth Day of April, 2016

Michelle K. Lee  
*Director of the United States Patent and Trademark Office*

SEQUENCE LISTING

```
<160> NUMBER OF SEQ ID NOS: 2

<210> SEQ ID NO 1
<211> LENGTH: 0
<212> TYPE: DNA
<213> ORGANISM: Homo sapiens

<400> SEQUENCE: 1

000

<210> SEQ ID NO 2
<211> LENGTH: 2868
<212> TYPE: DNA
<213> ORGANISM: Homo sapiens

<400> SEQUENCE: 2
cgaccgggac ggcccgtttt ccgccagctc gccgctcgct atggcgtcgc tcaccgtgaa      60
ggcctacctt ctgggcaagg aggacgcggc gcgcgagatt cgccgcttca gcttctgctg     120
```

-continued

```
cagccccgag cctgaggcgg aagccgaggc tgcggcgggt ccgggaccct gcgagcggct    180
gctgagccgg gtggccgccc tgttccccgc gctgcgcgcc ggcggcttcc aggcgcacta    240
ccgcgatgag gacggggact tggttgcctt ttccagtgac gaggaattga caatggccat    300
gtcctacgtg aaggatgaca tcttccgaat ctacattaaa gagaaaaaag agtgccggcg    360
ggaccaccgc ccaccgtgtg ctcaggaggc gccccgcaac atggtgcacc ccaatgtgat    420
ctgcgatggc tgcaatgggc tgtggtagg  aacccgctac aagtgcagcg tctgcccaga    480
ctacgacttg tgtagcgtct gcgagggaaa gggcttgcac cggggcaca  ccaagctcgc    540 attccccagc cccttcgggc acctgtctga gggcttctcg cacagccgct ggctccggaa    600
ggtgaaacac ggacacttcg ggtggccagg atgggaaatg gtccaccag  gaaactggag    660 cccacgtcct cctcgtgcag gggaggcccg ccctggcccc acggcagaat cagcttctgg    720
tccatcggag gatccgagtg tgaatttcct gaagaacgtt ggggagagtg tggcagctgc    780
ccttagcccc tgggcattg  aagttgatat cgatgtggag cacggaggga aaagaagccg    840
cctgaccccc gtctctccag agagttccag cacagaggag aagagcagct cacagccaag    900
cagctgctgc tctgacccca gcaagccggg tgggaatgtt gagggcgcca cgcagtctct    960
ggcggagcag atgaggaaga tcgccttgga gtccgagggg cgccctgagg aacagatgga   1020
gtcggataac tgttcaggag gagatgatga ctggacccat ctgtcttcaa agaagtggaa   1080
cccgtctaca ggtgaactcc agtccctaca gatgccagaa tccgaagggc aagctctct    1140 ggaccctcc  caggagggac ccacagggct gaaggaagct gccttgtacc acatctcccc   1200
gccagaggct gacccgcggc tgattgagtc cctctcccag atgctgtcca tgggcttctc   1260
tgatgaaggc ggctggctca ccaggctcct gcagaccaag aactatgaca tcggagcggc   1320
tctggacacc atccagtatt caaagcatcc cccgccgttg tgaccacttt tgcccacctc   1380
ttctgcgtgc ccctcttctg tctcatagtt gtgttaagct tgcgtagaat tgcaggtctc   1440
tgtacgggcc agtttctctg ccttcttcca ggatcagggg ttagggtgca agaagccatt   1500
tagggcagca aaacaagtga catgaaggga gggtccctgt gtgtgtgtgt gctgatgttt   1560
cctgggtgcc ctggctcctt gcagcagggc tgggcctgcg agacccaagg ctcactgcag   1620
cgcgctcctg accccctccct gcaggggcta cgttagcagc ccagcacata gcttgcctaa   1680 tggcttttcac ttttctctttt gttttaaatg actcataggt ccctgacatt tagttgatta   1740
ttttctgcta cagacctggt acactctgat tttagataaa gtaagcctag gtgttgtcag   1800
caggcaggct ggggaggcca gtgttgtggg cttcctgctg ggactgagaa ggctcacgaa   1860
gggcatccgc aatgttggtt tcactgagag ctgcctcctg gtctcttcac cactgtagtt   1920
ctctcatttc caaccatca  gctgctttta aaataagatc tctttgtagc catcctgtta   1980
aatttgtaaa caatctaatt aaatggcatc agcactttaa ccaatgacgt ttgcatagag   2040
agaaatgatt gacagtaagt ttattgttaa tggttcttac agagtatctt taaaagtgcc   2100
ttaggggaac cctgtccctc ctaacaagtg tatctcgatt aataacctgc cagtcccaga   2160
tcacacatca tcatcgaagt cttccccagt tataaagagg tcacatagtc gtgtgggtcg   2220
aggattctgt gcctccagga ccaggggccc accctctgcc cagggagtcc ttgcgtccca   2280
tgaggtcttc ccgcaaggcc tctcagaccc agatgtgacg gggtgtgtgg cccgaggaag   2340
ctggacagcg gcagtgggcc tgctgaggcc ttctcttgag gcctgtgctc tgggggtccc   2400
ttgcttagcc tgtgctggac cagctggcct ggggtccctc tgaagagacc ttggctgctc   2460
actgtccaca tgtgaacttt ttctaggtgg caggacaaat cgcgcccatt tagaggatgt   2520
```

-continued

```
ggctgtaacc tgctggatgg gactccatag ctccttccca ggaccctca gctcccggc    2580 actgcagtct gcagagttct cctggaggca ggggctgctg ccttgtttca ccttccatgt    2640
caggccagcc tgtccctgaa agagaagatg gccatgccct ccatttgtaa gaacaatgcc    2700
agggcccagg aggaccgcct gccctgcctg ggccttggct gggcctctgg ttctgacact    2760
ttctgctgga agctgtcagg ctgggacagg ctttgatttt gagggttagc aagacaaagc    2820
aaataaatgc cttccacctc accgcaaaaa aaaaaaaaa aaaaaaaa                 2868
```